United States Patent [19]

Hara

[11] Patent Number: 4,894,786

[45] Date of Patent: Jan. 16, 1990

[54] SIGNAL PROCESSING METHOD FOR ANALYZING AUTORADIOGRAPH

[75] Inventor: Makoto Hara, Minami-ashigara, Japan

[73] Assignee: Fuji Photo Film Co., Ltd., Minami-ashigara, Japan

[21] Appl. No.: 140,222

[22] Filed: Dec. 31, 1987

[30] Foreign Application Priority Data

Jan. 6, 1987 [JP] Japan ................................. 62-897

[51] Int. Cl.$^4$ ........................ G06F 15/42; C12Q 1/68; C12N 15/00
[52] U.S. Cl. ............................... 364/497; 364/413.01; 435/6; 436/94; 935/77
[58] Field of Search ............... 364/413.01, 496, 497; 435/6; 250/303, 484.1 B, 327.2 A, 327.2 C, 327.2 D; 935/77; 436/94

[56] References Cited

U.S. PATENT DOCUMENTS

| | | | |
|---|---|---|---|
| 4,617,468 | 10/1986 | Shiraishi et al. | 250/327.2 A |
| 4,629,891 | 12/1986 | Nakajima et al. | 250/484.1 B |
| 4,665,312 | 5/1987 | Shiraishi et al. | 250/327.2 D |
| 4,706,192 | 11/1987 | Nasu et al. | 364/413.01 |
| 4,720,786 | 1/1988 | Hara | 364/413.01 |
| 4,734,581 | 3/1988 | Hashiue | 250/327.2 C |
| 4,748,326 | 5/1988 | Mori et al. | 250/484.1 B |
| 4,777,597 | 10/1988 | Shiraishi et al. | 364/413.01 |

*Primary Examiner*—Parshotam S. Lall
*Assistant Examiner*—Kevin J. Teska
*Attorney, Agent, or Firm*—Sixbey, Friedman, Leedom & Ferguson

[57] ABSTRACT

A signal processing method for analyzing an autoradiograph to identify the locations of radioactively labeled substances which have been resolved in a one-dimensional developing direction on a support medium is provided. According to this method, digital image data including a plurality of different levels and values obtained by placing the support medium and a radiographic film together in layers to record the autoradiograph of the radioactively labeled substances are subjected to digital signal processing to identify their positions in a manner which substantially eliminates background noise. A stimulable phosphor sheet can be used in place of the radiographic film to record the autoradiograph. The method described herein may be effectively used to identify selected components of various biopolymers.

8 Claims, 5 Drawing Sheets y

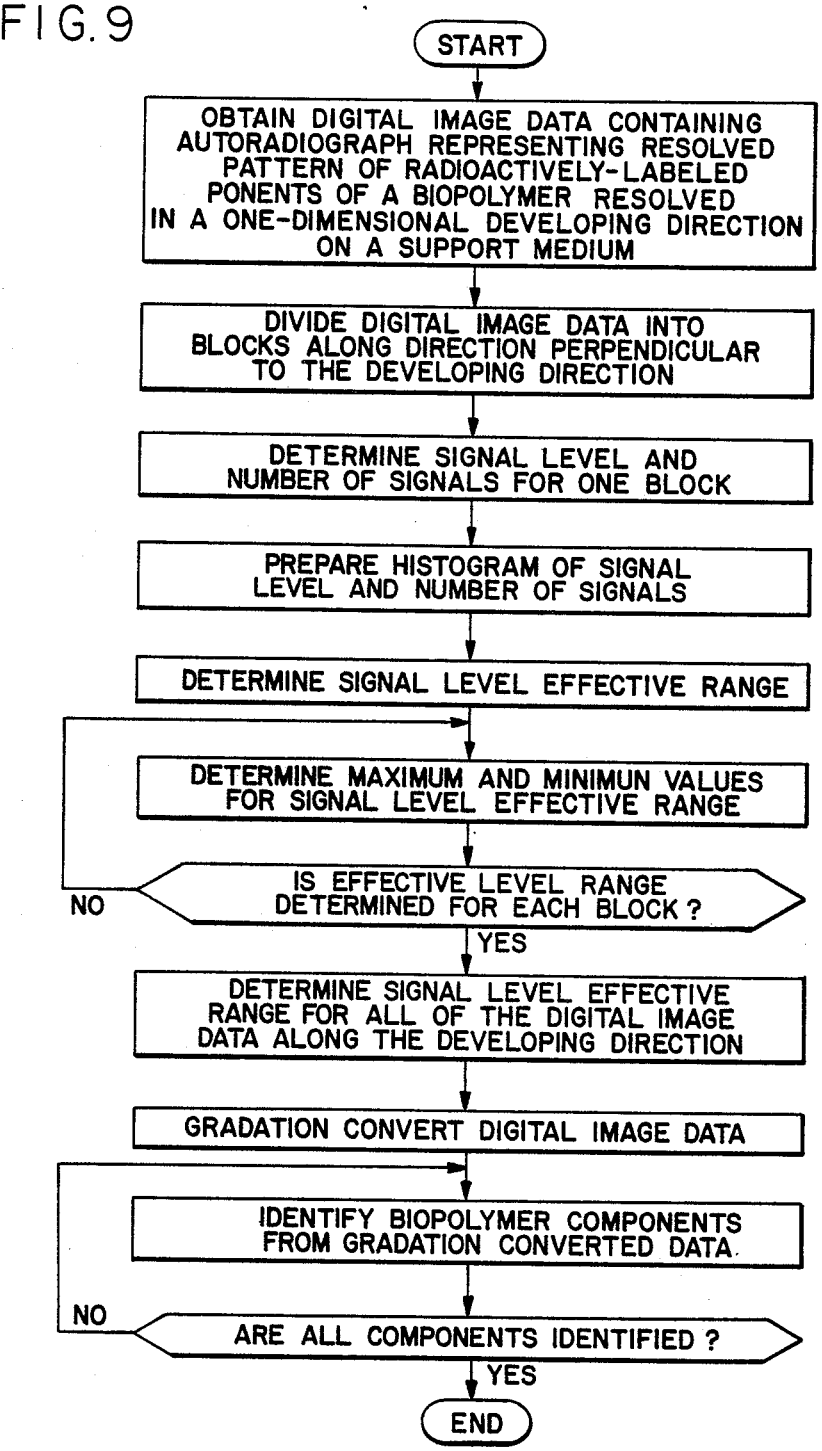

SIGNAL PROCESSING METHOD FOR ANALYZING AUTORADIOGRAPH

BACKGROUND OF THE INVENTION

1. Field of the Invention

This invention relates to a signal processing method for analyzing an autoradiograph.

2. Description of Prior Art

It is known that autoradiography can be used as a method for obtaining locational information on radioactively labeled substances distributed at least in one-dimensional direction on a support medium.

For instance, there is known an autoradiography comprising steps of: labeling organism-originating biopolymers such as proteins and nucleic acids with a radioactive element; resolving the mixture of the radioactively labeled biopolymers, derivatives thereof, cleavage products or synthetic products thereof on a gel support (medium) through a resolving process such as gel electrophoresis; placing the gel support medium and a high-sensitivity X-ray film together in layers for a certain period of time to expose said film to the gel support, and then performing the isolation and identification of the polymeric substances, determination of molecular weight of the polymeric substances and evaluation of characteristics of the polymeric substances based on the obtained locational information of the radioactively labeled substances from the exposed part of the film.

Recently, the autoradiography has been effectively used especially for determining the base sequence of nucleic acids such as DNA and RNA. Further, the autoradiography is an essential means for the screening of genes using a hybridization process such as Southern blotting, Northern blotting or colony hybridization.

For the purpose of simply carrying out the determination of the base sequence of nucleic acids with high accuracy in said autoradiography, there are described in co-pending U.S. patent application Nos. 664,405 (now abandoned) and 837,037 (now abandoned) autoradiographic procedures which utilize a radiation image recording and reproducing method using a stimulable phosphor sheet in place of the above-mentioned conventional radiography using a radiosensitive material. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no trouble of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to an image.

The analysis of an autoradiograph has been conventionally made by visually judging each of the resolved portions (bands) of the radioactively labeled substances on a visualized autoradiograph, thus obtaining locational information on the radioactively labeled specific substances (and identification of biopolymers, determination of molecular weight and evaluation of characteristics of biopolymers based on the obtained locational information of the radioactively labeled substances). For instance, the base sequence of the nucleic acids has been conventionally determined by visually comparing the positions of the bands of the mixture of the base-specific fragments of the nucleic acids such as DNA and RNA. Thus, the analysis of the autoradiograph requires great amounts of time and labor.

Further, since the visual analysis of the autoradiograph varies or fluctuates owing to the skill of investigators, the results on the determination of the base sequence of the nucleic acid vary depending on the investigators and the accuracy of information is limited to a certain extent.

In order to improve the accuracy of information, there are proposed in co-pending U.S. patent application Nos. 568,877 (now abandoned), 730,034 (now abandoned) 917,606 and 917,609 methods for automatically obtaining locational information on the radioactively labeled substances in the form of numerals and/or symbols by obtaining the autoradiograph as digital signals and subjecting the digital signals corresponding to the autoradiograph can be obtained either by visualizing the autoradiograph on a radiographic film and photoelectrically reading out the visible image on said film by means of reflected light or transmitted light when the conventional radiography is used, or by directly reading out the stimulable phosphor sheet without the visualization of the autoradiograph when the radiation image recording and reproducing method is used.

However, the resolved pattern obtained by resolving (developing) radioactively labeled substances on a support medium by electrophoresis or the like is liable to cause various distortion and noise.

For instance, when the autoradiograph of the resolved pattern obtained by electrophoresing base-specific DNA fragments to determine the base sequence of DNA is illustrated in the form of a kind of a bird's-eye view (a view obtained by superposing a number of waveforms composed of a position and a signal level along the developing direction), there can be obtained FIG. 2 wherein background noise is very large and the positions of intrinsic bands can be scarcely determined. FIG. 2 is such a bird's-eye view showing the autoradiograph of the resolved pattern, wherein the developing direction is in the y-direction.

The background noise is produced, when a sample is contaminated with radioactive impurities by poor labeling of the base-specific DNA fragments with a radioactive element in the course of the preparation of the sample, or when a stimulable phosphor sheet or a radiosensitive material is exposed to a natural radiation.

Accordingly, it is desirable to provide an image suitable for analysis by simply eliminating such noise in the cases of the automatic analysis of the autoradiograph by digital signal processing as well as the analysis of the autoradiograph by visually judging the visualized image.

SUMMARY OF THE INVENTION

The present inventor has discovered that noise can be easily eliminated with high accuracy by subjecting digital image data containing a autoradiograph of a resolved pattern to appropriate signal processing in the analysis of an autoradiograph having information on the one-dimensional or two-dimensional location of radioactively labeled substances.

The present invention provides a signal processing method for analyzing an autoradiograph by subjecting digital image data containing an autoradiograph of a resolved pattern to digital signal processing to obtain information on the location of radioactively labeled substances in the form of numerals and/or symbols. The resolved pattern is formed by resolving radioactively labeled substances in a one-dimensional developing direction on a support medium. The present digital signal processing method includes the steps of dividing the digital image data into two or more blocks along a direction perpendicular to the developing direction; determining the signal level and the number of signals for each of the blocks; and preparing a histogram representative of the relationship between signal level and number of signals for each of the blocks. The histogram is then used to determine an effective range of the signal level and maximum and minimum values of this effective range of the signal level. An effective level range over all of the digital image data at every position along the developing direction is then determined on the basis of the effective level range determined for each block. This effective level range is used to convert the digital image data to produce a gradation of digital signals dependent on the maximum and minimum signal values determined from the histogram. The positions of the radioactively labeled substances on the support medium are then identified from these gradation converted digital signals.

In the present invention, the term "locational information" of the radioactively labeled substances includes a variety of information relating to the location of the radioactively labeled substances, or the aggregation thereof, such as the position and shape of the aggregation of radioactive substances present in the sample, the concentration and distribution of the radioactive substances on the position, and combination thereof.

According to the present invention, positions where intrinsic bands exist can be clearly determined by eliminating noise, particularly background noise caused on the autoradiograph of a resolved pattern. Further, the separability of bands increases and every band is made clear by the signal processing of the present invention, even when two or more bands are combined together or poorly separated from each other.

In the Sanger-Coulson method, the amount of a radioactive element is increased and the intensity of radioactivity becomes higher in proportion as the molecular weight of the base-specific fragments of the sample increases. There is produced on the autoradiograph a density gradient (i.e., variation of signal level) that the image density lowers as the migration distance becomes greater. Even when signal level varies depending on the resolved positions as in the case described above, gradation conversion according to the signal level of the resolved position can be conducted by setting an effective level range from each block. Thus, there is no trouble eliminating an intrinsic band and there is no possibility that noise is insufficiently or locally eliminated. Hence, each of intrinsic bands is made clear. Further, since the effective level ranges are interpolated between the blocks and are continuous, there is not caused a great difference in the densities of images obtained by gradation conversion between the blocks, so that there can be obtained image which have uniformity in density and can be easily analyzed.

Accordingly, when the autoradiograph is visualized on the basis of the digital image data obtained by gradation conversion, the relationship between the respective positions of the bands can be easily judged from the visible image. When the autoradiograph is automatically analyzed by subjecting the digital image data to signal processing, the bands can be easily detected with high accuracy and the relationship between the positions thereof can be determined.

BRIEF DESCRIPTION OF DRAWINGS

FIG. 9 is a flowchart representing the process of the present invention.

DETAILED DESCRIPTION OF THE INVENTION

Figure 1:
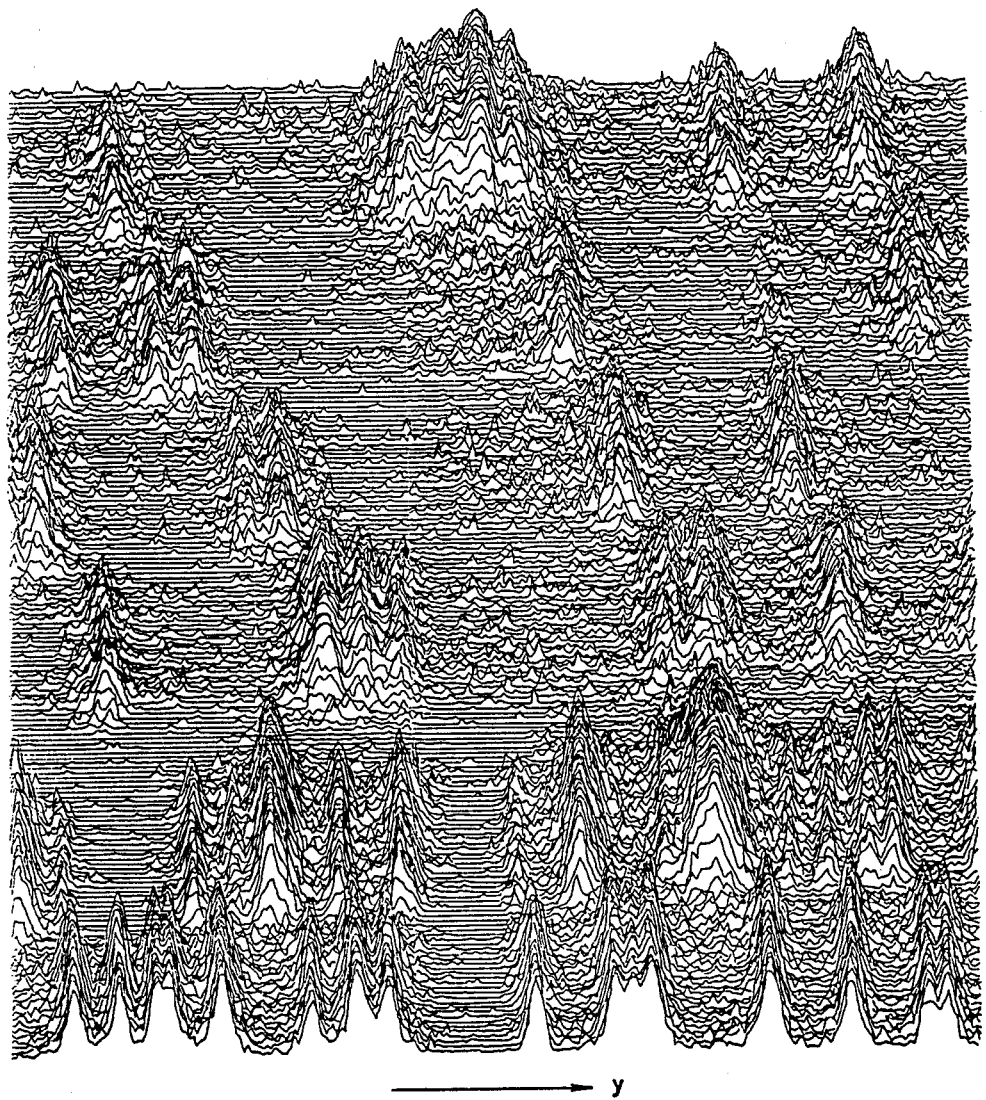
FIG. 1 is a view showing an autoradiographic view (a bird's-eye view) obtained by subjecting an image of FIG. 2 to gradation conversion according to the present invention.

Examples of samples employable in the present invention include organism-originating biopolymers such as protein, nucleic acids, derivatives thereof, cleavage fragments thereof and synthetic products thereof, which are labeled with a radioactive element.

Typical examples thereof are mixtures of base-specific fragments of nucleic acids such as DNA and RNA labeled with a radioactive element. The term "fragments" of nucleic acids means a plurality of different portions of a long-chain molecule. For instance, a mixture of base-specific DNA cleavage products, which is a kind of a mixture of base-specific DNA fragments, can be obtained by base-specifically cleaving the radioactively labeled DNA according to the Maxam-Gilbert method. A mixture of base-specific DNA synthetic products can be obtained by synthesizing from radioactively labeled deoxynucleoside triphosphates and DNA polymerase by the use of DNA as a template according to the Sanger-Coulson method. Mixtures of base-specific RNA fragments can be also obtained as a mixture of cleavage products or a mixture of synthetic products in a similar manner to the DNA method. DNA is composed of four kinds of bases: adenine, guanine, thymine and cytosine as its constitutional units, and RNA is composed of four kinds of bases: adenine, guanine, uracil and cytosine.

These substances can be labeled with a radioactive element such as $^{32}P$, $^{14}C$, $^{35}S$, $^{3}H$ or $^{125}I$ by any of appropriate method.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital image data containing the autoradiograph of the radioactively labeled substance is then obtained through an appropriate read-out system.

When the conventional radiography is used, the support medium and a radiosensitive material such as an X-ray film are placed together in layers at a low temperature or at room temperature for a long period of time (several hours to several tens of hours) to give exposure to the radiographic film. The radiographic film is then developed to visualize the autoradiograph of the radioactively labeled substances on the film, and the visualized autoradiograph is read out using an image read-out system. For instance, the radiographic film is irradiated with optical beam and a beam transmitted or reflected is photoelectrically detected, whereby the visualized autoradiograph can be transformed into electric signals. Further, the electric signals are converted into digital image data through A/D conversion.

When the radiation image recording and reproducing method is used, the support medium and the stimulable phosphor sheet are placed together in layers at an ambient temperature for a short period of time (several seconds to several tens of minute) to store radiation energy radiating from the radioactively labeled substances in the phosphor sheet, whereby the autoradiograph is recorded as a kind of a latent image (energy-stored image) on the phosphor sheet. The stimulable phosphor sheet, for example, has a basic structure where a support such as a plastic film, a phosphor layer comprising a stimulable phosphor such as a divalent europium activated barium fluorobromide phosphor ($BaFBr:Eu^{2+}$) and a transparent protective film are laminated in order. The stimulable phosphor has characteristics of absorbing and storing radiation energy when irradiated with a radiation such as X-rays and subsequently releasing the stored radiation energy as stimulated emission when excited with visible light to infrared rays.

Then, the autoradiograph stored and recorded on the stimulable phosphor sheet is read out using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without visualization thereof. Further, the electric signals are converted into digital image data containing the autoradiograph through A/D conversion. The above-described methods for measuring the autoradiograph and obtaining the digital image data containing the autoradiograph are described in more detail in the aforementioned U.S. patent application Nos. 568,877 (now abandoned) and 837,037.

In the above read-out procedures, it is not always necessary to conduct the read-out operation of the autoradiograph all over the surface of the radiographic film or the stimulable phosphor sheet. Only the image region may be subjected to the read-out operation.

While the methods for obtaining the digital image data containing the autoradiograph of the radioactively labeled substances resolved on a support medium using the conventional radiography and the radiation image recording and reproducing method are described above, the present invention is not limited thereto and digital image data obtained by any other method can be applied to the signal processing method of the invention, provided that they contain the autoradiograph.

The obtained digital image data are a set of digital signals $D_{xy}$ defined by coordinates (x,y) which are represented by a coordinate system fixed to the radiographic film or the stimulable phosphor sheet and signal level (z) at the coordinate. The signal level represents the density of image at the coordinate, that is, the amount of the radioactively labeled substances. Accordingly, the digital image data have information on two-dimensional location of the radioactively labeled substances.

The thus-obtained digital image data containing the autoradiograph of the radioactively labeled substances resolved on a support medium is subjected to signal processing to analyze the autoradiograph according to the present invention described in more detail below.

The signal processing method of the present invention will be described by referring to an example of an electrophoretic pattern of electrophoretic rows (resolved rows) which are formed by resolving (developing) a sample on a support medium by electrophoresis, said sample being composed of a combination of the following four groups of base-specific DNA fragments labeled with a radioactive element:

(1) guanine (G)—specific DNA fragments,
(2) adenine (A)—specific DNA fragments,
(3) thymine (T)—specific DNA fragments,
(4) cytosine (C)—specific DNA fragments.

Each group of the base-specific DNA fragments is composed of DNA fragments which are synthesized according to the Sanger-Coulson method and have various lengths and the same base at terminals.

The digital image data containing the autoradiograph of the base-specific DNA fragments are stored temporarily in a memory device of a signal processing circuit (that is, stored in a nonvolatile memory unit such as a buffer memory, a magnetic disk, etc.).

Usually, the digital image data obtained by reading out the radiographic film or the stimulable phosphor sheet contain image information on the whole surface of the film or the phosphor sheet including the electrophoretic pattern. Namely, the digital image data contains extra digital data in addition to the data of the image region (pattern region). Accordingly, it is desirable that only image data corresponding to the image region are extracted from the resulting digital image data (that is, the draw-out of image region) from the viewpoints of improving the gradation conversion processing in quality and also improving processing efficiency before the digital image data are subjected to the gradation conversion processing.

For instance, the image data corresponding to the electrophoretic pattern can be extracted by the following signal processing. The resulting image data are divided into two or more blocks along a direction (x-direction) perpendicular to the developing direction, and there is then made an addition of the image data along the developing direction (y-direction) for every block to obtain a one-dimensional waveform (projection) composed of positions in the x-direction and signal level. The boundary of the electrophoretic pattern region and further the boundary of each resolved row (lane) are detected from the projection for every block. These boundaries are interpolated between the blocks, whereby the boundaries are interpolated between the blocks, whereby the boundaries of the whole electrophoretic region and the whole lanes in the width direction (x-direction) can be determined. In a similar manner to that described above, the boundaries in the lengthwise direction (y-direction) can be determined.

The above-described signal processing method for drawing out said image region is described in more detail in our co-pending U.S. patent application Ser. No. 138,395 filed on December 28, 1987.

Alternatively, the electrophoretic pattern region can be input as information by electrically displaying the autoradiograph on the basis of the digital image data on a screen such as CRT and then operating display image with a mounse cursor on the screen or making keyboard operation.

Since the positions of the boundaries in the lengthwise direction can be approximately identified by the positions (slots) of the introduction of a sample and electrophoretic conditions, the positions may be previously set as fixed coordinates.

Figure 3:
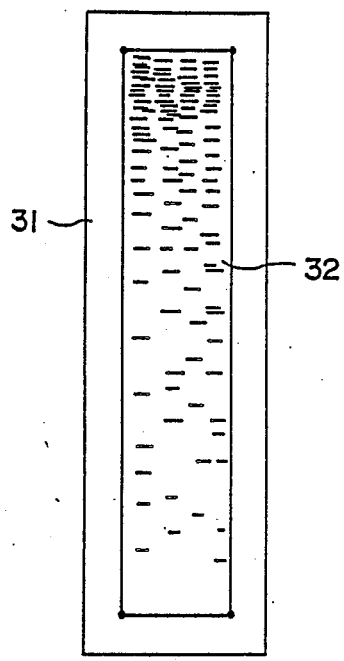
FIG. 3 shows an example of an image on the basis of digital image data including an autoradiograph of an electrophoretic pattern.

FIG. 3 shows an example of an autoradiographic image when the resulting digital image data as such are visualized as an image. Image data corresponding to the electrophoretic region 32 are extracted from the whole image 31.

Figures 4, 5, 7:
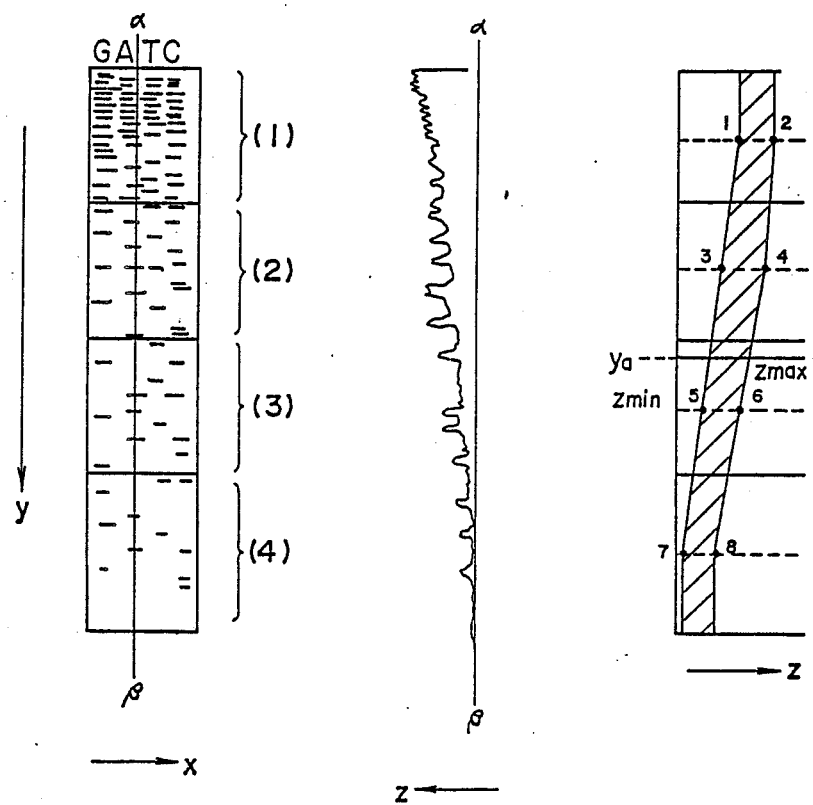
FIG. 4 shows an example of an autoradiographic image in an electrophoretic pattern region which is formed by visually extracting digital image data.
FIG. 5 shows a one-dimensional waveform (cross-sectional image) composed of positions and signal level (z) along the y-direction obtained by extracting image data along the line $\alpha$—$\beta$ in FIG. 4.
FIG. 7 shows schematically an example of an operation for determining effective level range over the whole of an electrophoretic pattern.

FIG. 4 shows an example of an autoradiographic image in the electrophoretic pattern region when the extracted digital image data are visualized as an image. The electrophoretic pattern is composed of four lanes corresponding to the sample.

FIG. 5 shows a one-dimensional waveform (cross-sectional image) composed of positions and signal level (z) along the y-direction obtained by extracting image data along the line $\alpha-\beta$ in FIG. 4. The signal level becomes gradually higher as the position becomes nearer the electrophoresis-starting position. Thus, a density gradient is produced.

The digital image data containing image information as shown in FIG. 4 are divided into two or more blocks along a direction perpendicular to the developing direction. The term "developing direction" is intended not to mean an actual electrophoretically developing direction in the strict sense, but to mean a direction intended to be electrophoresed, that is, the major axis direction (y-direction) of the support medium (that is, a radiographic film or a stimulable phosphor sheet).

The number of the blocks obtained by dividing the image data varies depending on the type of the sample, the number of the bands, the amount of the data and the change of signal level (density gradient), but is preferably 4 to 6.

When the image data are divided into plural blocks along a direction (x-direction) perpendicular to the developing direction and subjected to the following operational processing, effective level range can be accurately determined according to image density, even when a density gradient is produced.

In FIG. 4, the image data are divided into four blocks of (1) to (4).

Subsequently, histogram representing the relationship between signal level and the number of signals is prepared for every block.

Figure 6:
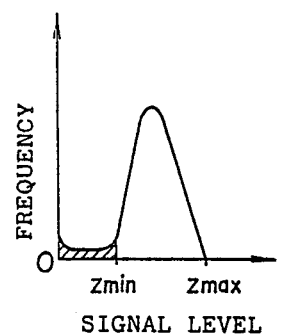
FIG. 6 is a graph showing histogram.

FIG. 6 is a graph showing the histogram of the first block, wherein the abscissa axis represents signal level and the ordinate axis represents the number of signals (frequency).

The calculation of the histogram may be made for the whole image data within one block, or for a part of the image data. When only a part of the image data is used, data may be extracted along the line $\alpha-\beta$ in FIG. 4.

Then, the maximum value and the minimum value of the effective range of signal level are determined from the histogram for every block.

In the histogram of FIG. 6, the search is started from the higher side of signal level, there is found out a point ($Z_{max}$) where the number of signals does not become zero first and the point is referred to as the maximum value of the effective level range (effective density range).

The minimum value of the effective level range can be determined by presetting a ration of the area of a region ranging from zero of signal level to the minimum value thereof (the area of the shaded portion of FIG. 6) to the whole area of the histogram as threshold value, starting a search from the lower side of signal level and finding out a point ($Z_{min}$) where the area ratio is equal to the threshold value. The area ratio to be preset as the threshold value varies depending on the radiation intensity of the sample, the degree of background noise, etc., but is generally in the range of 10 to 20%. The threshold value may vary with the block. In this way, the effective level range can be determined for every block.

The effective level range over the whole of the digital image data is then determined along the developing direction by interpolating the effective level ranges of the blocks.

Figure 2:
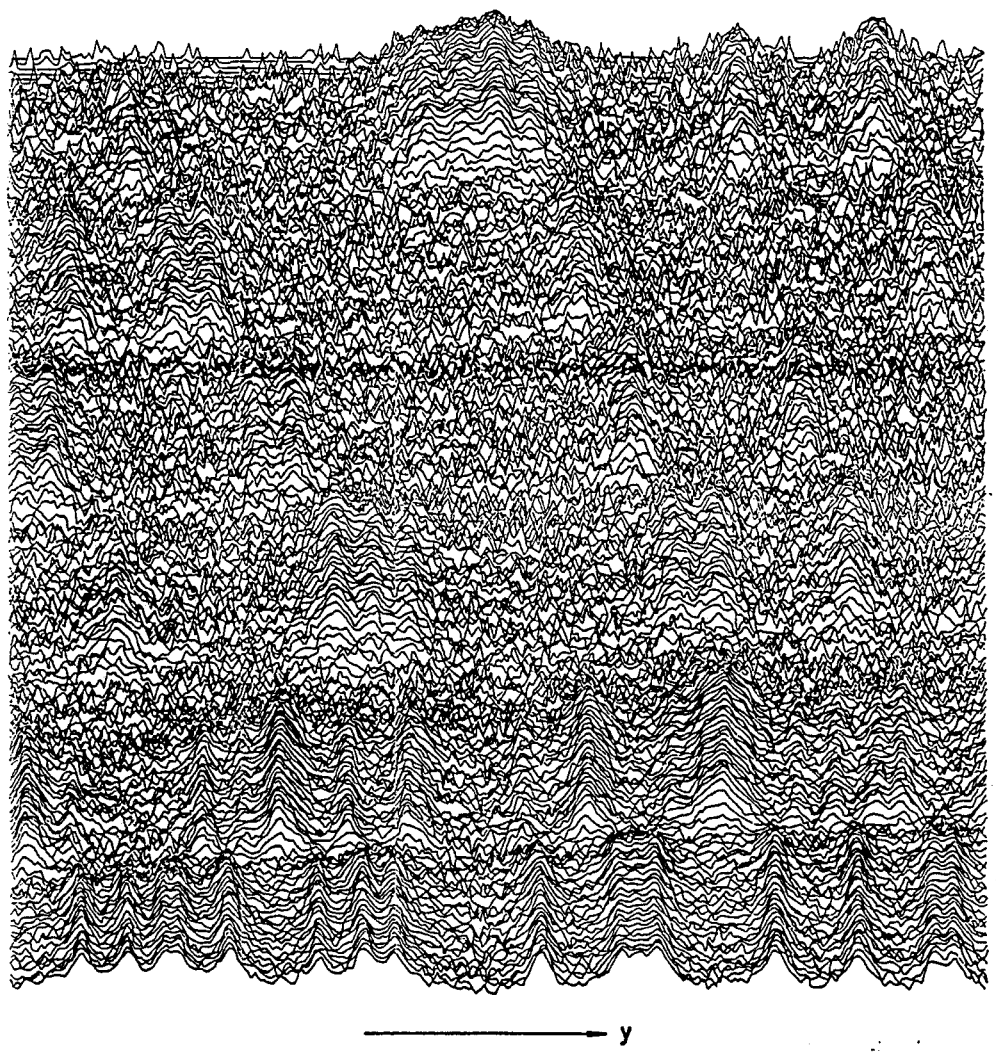
FIG. 2 is a view showing an autoradiographic image (a bird's-eye view) of an electrophoretic pattern having been treated with no gradation conversion processing.

For instance, the effective level range of the first block designated by $Z_{min}$ and $Z_{max}$ in FIG. 6 is fixed on the central line which divides the first block in two along the x-direction as shown in FIG. 2.

FIG. 7 shows schematically an example of an operation for determining the effective level range over the whole of the electrophoretic pattern.

In a similar manner to that described above, the determined effective level range of each of the remaining blocks is fixed on the central line. The minimum and maximum values of these blocks are then connected to each other in order, respectively to make linear interpolation, whereby there can be determined the effective level range (the shaded portion of FIG. 7) which continuously varies with the electrophoretic positions.

Subsequently, the digital image data are subjected to gradation conversion according to the effective level range.

Since the effective level range varies with the electrophoretic positions (in y-coordinate), the gradation conversion of the image data is made on the basis of the effective level range according to the y-coordinate of digital signals.

Figure 8:
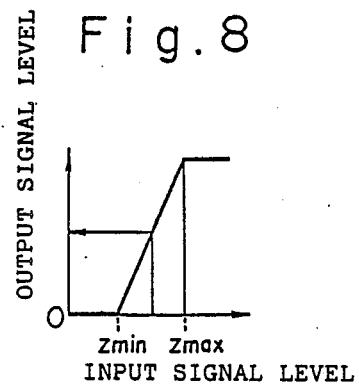
FIG. 8 is a graph showing an example of gradation conversion.

FIG. 8 is a graph showing an example of gradation conversion at the position $y_a$ in the developing direction, wherein the abscissa axis represents input signal level and the ordinate axis represents output signal level.

For instance, the image data at the position $y_a$ in the developing direction are converted in the following manner as shown in FIG. 8.

(1) When signal level is not higher than the minimum value ($Z_{min}$) of the effective level range, the image data are uniformly converted into zero level $[Z \leq Z_{min} \to Z=0]$.

(2) When signal level is higher than the minimum value ($Z_{min}$), but lower than the maximum value ($Z_{max}$), the image data are linearly converted in proportion to said signal level $[Z_{min} < Z < Z_{max} \to Z=f(z)]$.

(3) When signal level is not lower than the maximum value ($Z_{max}$) of the effective level range, the image data are uniformly converted into the maximum output level $[Z_{max} \leq Z \to Z=Z'max]$.

In this way, all image data are subjected to different gradation conversion varying with y-coordinates, whereby noise can be eliminated.

FIG. 1 shows an autoradiographic image obtained by subjecting an image of FIG. 2 to gradation conversion according to the present invention. It is apparent from FIG. 1 that background noise is properly eliminated by the gradation conversion processing of the present invention, so that high and low grounds are made clear where bands exist or not and the positions of the bands can be judged easily and accurately.

FIG. 9 illustrates a flowchart representative of the steps of the present process.

In the above-described embodiment, the gradation conversion processing is conducted with an electrophoretic pattern unit by lumping four lanes together. However, the gradation conversion processing can be conducted for every lane, if desired. Namely, gradation conversion can be conducted for not only electrophoretic position (i.e., position of development), but also each lane by drawing out each lane before the division of the digital image data into blocks, and subjecting each of the drawn-out lanes to the above-described operation. This processing is a preferred method, when the amount of a sample such as base-specific DNA fragments varies depending on slots.

The digital image data after the above gradation conversion by signal processing are output from a signal processing circuit and subsequently transmitted to a display recording device directly or optionally via storage in a storing means such as a magnetic disk or a magnetic tape. If desired, the image data are further transmitted to other signal processing circuit.

Various display devices can be used, for instance, graphic display for non-gradation, electrical devices such as CRT. Various recording devices can be used, for instance, graphic dot printer, a device for visualizing image optically by scanning a photosensitive material with laser beam, a display means for visualizing electrically image on CRT, a means for printing a radiation image displayed on CRT by means of a video printer and a means for visualizing image on heatsensitive recording material using thermic rays. The base sequence of DNA can be determined easily and accurately by visually judging on a display screen or a recording paper an autoradiographic image from which noise has been eliminated.

When the autoradiograph is automatically analyzed by signal processing, the base sequence of DNA can be automatically determined with high accuracy by detecting bands in a processing circuit having a proper signal processing function and comparing the positions of the bands among the lanes.

In the above-described example, there has been described the case where one electrophoretic pattern composed of four lane is used, but the present invention is by no means limited thereto, and the method of the present invention can also be applied to the cases where two or more electrophoretic patterns are used. Further, when the sample is a mixture of base-specific DNA fragments, the present invention is by no means limited to the exclusive combination described above, but other combination can be used. The sample of the present invention is not limited to the base-specific DNA fragments. The method of the present invention can be applied to various resolved patterns of radioactively labeled substances resolved in one-dimensional direction on a support medium by various resolving means. Particularly, the method of the present invention is suitable for use in carrying out the microanalysis of proteins as well as the screening of genes.

I claim:

1. A signal processing method for analyzing an autoradiograph to identify locations of radioactively labeled substances on a support medium, said labeled substances being resolved in a pattern along a one-dimensional developing direction on the support medium by subjecting to digital signal processing digital image data including a plurality of signals of different levels and values obtained by placing the support medium and a radiographic film together in layers to record the autoradiograph of the radioactively labeled substances on said radiographic film as a visible image, and photoelectrically reading out the autoradiograph visualized on the radiographic film, wherein said digital signal processing includes the steps of:

(a) dividing said digital image data into two or more blocks along a direction perpendicular to the developing direction;

(b) determining the signal level and the number of signals for each of said blocks;

(c) preparing a histogram representative of the relationship between signal level and number of signals for each of said blocks.

(d) determining an effective range of signal level and the maximum value and the minimum value of said effective range of signal level from said histogram;

(e) determining an effective level range over all of the digital image data at every position along the developing direction on the basis of the effective level range determined for each block;

(f) using the effective level range determined in step (e), converting the digital image data to produce a gradation of digital signals dependent on the maximum and minimum signal values determined in step (d); and (g) identifying the positions of the radioactively labeled substances on the support medium from the gradation converted digital signals produced in step (f).

2. The signal processing method as claimed in claim 1, wherein digital image data in step (a) are image data corresponding to one resolved row produced by extracting said image data corresponding to each resolved row before said step (a) and each of said steps (a) through (f) is repeatedly performed for every resolved row.

3. The signal processing method as claimed in claim 1, wherein said histogram is prepared for all image data within each block in the step (c).

4. The signal processing method as claimed in claim 1, wherein a part of the image data along the developing direction within the block is extracted and histogram is prepared on the basis of the extracted image data in the step (c).

5. The signal processing method as claimed in claim 1, wherein the higher side of the signal level is identified on the histogram, a ratio of the area of the effective level range to the whole area of the histogram is determined, and in step (d) the histogram is searched from the higher side of the signal level on the histogram to locate the maximum value of the effective level range, said maximum value being a point where the number of signals does not become zero first and the minimum value of the effective level range, said minimum value being a point where the ration of the area of the effective level range to the whole area of the histogram is equal to a threshold value.

6. The signal processing method as claimed in claim 1, wherein the effective level range of each block is fixed to a neutral point identified for each block and a linear interpolation is made for the effective level ranges of all blocks to determine the effective level ranges over the whole of the digital image data at every position along the developing direction in the step (e).

7. The signal processing method as claimed in claim 1, wherein the digital image data are subjected to gradation conversion at every position along the developing direction according to the effective level range at said position in such a manner that a signal level not higher than the minimum value of the effective level range is made to be zero, a signal level within the effective level range is linearly increased and a signal level not lower than the maximum value of the effective level range is made to be the maximum constant level in the step (f).

8. A signal processing method for analyzing an autoradiograph to identify locations of radioactively labeled substances on a support medium, said labeled substances being resolved in a pattern along a one-dimensional developing direction on the support medium by subjecting to digital signal processing digital image data including a plurality of signals of different levels and values obtained by placing the support medium and a stimulable phosphor sheet comprising a stimulable phosphor together in layers to record the autoradiograph of radioactively labeled substances on said phosphor sheet, irradiating said phosphor sheet with stimulating rays and photoelectrically detecting the autoradiograph as stimulated emission, wherein said digital signal processing includes the steps of:

(a) dividing said digital image data into two or more blocks along a direction perpendicular to the developing direction;

(b) determining the signal level and the number of signals for each of said blocks;

(c) preparing a histogram representative of the relationship between signal level and number of signals for each of said blocks, (d) determining an effective range of signal level and the maximum value and the minimum value of said effective range of signal level from said histogram;

(e) determining an effective level range over all of the digital image data at every position along the developing direction on the basis of the effective level range determined for each block;

(f) using the effective level range determined in step (e), converting the digital image data to produce a gradation of digital signals dependent on the maximum and minimum signal value determined in step (d); and, (g) identifying the positions of the radioactively labeled substances on the support medium from the gradation converted digital signals produced in step (f).

* * * * *